United States Patent

Simonetti

[11] Patent Number: 6,073,042
[45] Date of Patent: Jun. 6, 2000

[54] DISPLAY OF THREE-DIMENSIONAL MRA IMAGES IN WHICH ARTERIES CAN BE DISTINGUISHED FROM VEINS

[75] Inventor: Orlando P. Simonetti, Naperville, Ill.

[73] Assignee: Siemens Medical Systems, Inc., Iselin, N.J.

[21] Appl. No.: 08/937,952

[22] Filed: Sep. 25, 1997

[51] Int. Cl.⁷ ................................................ A61B 5/055
[52] U.S. Cl. ........................ 600/420; 324/307; 324/309
[58] Field of Search ........................... 60/410, 420, 419; 324/307, 309

[56] References Cited

U.S. PATENT DOCUMENTS

| | | | |
|---|---|---|---|
| 5,792,056 | 8/1998 | Prince | 600/420 |
| 5,799,649 | 9/1998 | Prince | 128/653.2 |
| 5,924,987 | 7/1999 | Meaney et al. | 600/420 |
| 5,928,148 | 7/1999 | Wang et al. | 600/420 |

*Primary Examiner*—Marvin M. Lateef
*Assistant Examiner*—Eleni Mantis Mercader
*Attorney, Agent, or Firm*—Mark H. Jay

[57] ABSTRACT

An intravascular MR contrast agent is administered to a living patient. A series of three-dimensional dynamic MR datasets is acquired from the Volume of Interest ("VOI"), beginning after administration of the contrast agent and continuing for a sufficiently long time as to reflect contrast agent enhancement of all arterial and venous blood vessels within the VOI. A three-dimensional MR angiogram of the VOI is acquired after the contrast agent has reached equilibrium. For each voxel within the VOI, enhancement of that voxel as a function of time post administration of the contrast agent is computed. Parameters that distinguish enhancement of voxels relating to the patient's arteries from enhancement of voxels relating to the patient's veins are selected, and the intensity of each voxel in the MR angiogram is scaled in accordance with the selected parameters. A maximum intensity projection reconstruction of the VOI is generated from the MR angiogram in which voxel intensity has been scaled.

9 Claims, 4 Drawing Sheets

DISPLAY OF THREE-DIMENSIONAL MRA IMAGES IN WHICH ARTERIES CAN BE DISTINGUISHED FROM VEINS

BACKGROUND OF THE INVENTION

The invention relates to magnetic resonance (MR), and more particularly relates to MR angiography (MRA). In its most immediate sense, the invention relates to three-dimensional MRA in which contrast agent is used.

In MRA, and particularly in three-dimensional MRA, it is advantageous for a clinician (usually a radiologist) to be able to distinguish arteries from veins. Existing methodology for doing this has proven unsatisfactory.

In conventional MRA (which does not use contrast agents), venous or arterial signals are selectively eliminated during image acquisition by presaturating the venous or arterial blood flow and thereby preventing it from producing an MR signal. The typical result is an MR angiogram depicting only arteries, or only veins. The effective shortening of the T1 relaxation time in blood which produces a high signal-to-noise ratio in contrast-enhanced MRA also causes such conventional presaturation techniques to fail. Because of this, to distinguish between arteries and veins, contrast-enhanced MRA data is typically acquired in two steps, the first being carried out to acquire an enhanced arterial image and the second being carried out when both arteries and veins are enhanced. The first image displays the arteries, and a subtraction image formed between the first image and the second image displays the veins. Each of these images must be acquired rapidly; the first image must capture the peak of the arterial bolus, and the second must be carried out before the venous enhancement diminishes, and in the case of conventional extravascular agents, before the surrounding tissue is significantly enhanced. Because each of the images must be acquired quickly, the images necessarily have low spatial resolution.

Because the subtraction image only relates to the state of the patient's circulatory system at two particular times, such a methodology provides only a limited capability of distinguishing between arteries and veins and is highly sensitive to the timing and speed of data acquisition relative to the injection of the contrast agent. If this timing is miscalculated, or if the acquisition lasts too long, the acquisition does not acquire a purely arterial phase, but rather a combination of arterial and venous phases together. Furthermore, if some veins have not yet enhanced by the time of the second acquisition, they will not appear in the subtracted image.

It would be advantageous to provide improved methodology for acquiring three-dimensional MRA data from a patient's arteries and veins within a volume of interest (VOI) and for displaying an image reconstructed from such data in which it would be possible to visually distinguish the arteries from the veins.

It is therefore an object of the invention to provide a method that would make it possible to distinguish arteries from veins in a three-dimensional MRA image.

The invention proceeds from the realization that by administering a bolus of an MR contrast agent into the patient's circulatory system and by tracking the position of the bolus as a function of time, it is possible to distinguish arteries from veins. This is because the bolus normally passes through the patient's circulatory system along a route that is known in advance, and the position of the bolus within the circulatory system can therefore in the normal case be correlated with time post administration. For this reason, the progress of the contrast agent through the patient's circulatory system as a function of time can therefore be used to distinguish arteries from veins. Indeed, even if the blood does not flow along the expected path (as can be the case when e.g. the patient's heart is malformed) the actual flow path can be mapped out as a function of time, thereby providing the physician with blood flow images that are outside conventional "venous" or "arterial" categories.

In accordance with the invention, this time-based information is used to scale the intensity of voxels in a three-dimensional MR image. Put another way, in accordance with the invention, for each voxel within the VOI, the enhancement of that voxel as a function of time is determined, and individual voxels in a three-dimensional MR image of the VOI are visually emphasized and de-emphasized in accordance with this determination and the requirements of the physician or technician.

The preferred embodiment of the invention further proceeds from the realization that if an intravascular contrast agent is used, a high resolution acquisition of longer duration can be run after the contrast agent has reached an equilibrium state in the bloodstream. The time-based information is used to scale the displayed intensities of voxels in a high-resolution MR angiogram, and the image intensities of individual voxels in the high-resolution MR angiogram can be manipulated so as to visually distinguish arteries from veins. While this scaling step is particularly advantageous because of the higher resolution of the diagnostic image, it is not necessary. Even without an intravascular contrast agent and a high-resolution MR angiogram, the time-based information is sufficient to characterize the path of blood flow and to thereby distinguish and depict arteries and veins.

In accordance with another of its aspects, the invention resides in a) administering a bolus of contrast agent to the patient's circulatory system in such a manner as to enhance the vascular structure, b) acquiring three-dimensional MR image data from the VOI in such a manner as to register, as a function of time, movement of the contrast agent through the vascular structure, c) scaling voxels in a three-dimensional MR image of the VOI in accordance with the individual sections to be selectively emphasized, and d) displaying the three-dimensional MR image using image values taken from the scaled acquired MR image data. Advantageously, a high-resolution three-dimensional MR image of the VOI is acquired after the contrast agent has reached equilibrium in the VOI, the scaling step is applied to the image data in the high-resolution three-dimensional MR image, and the displaying step includes the step of displaying a Maximum Intensity Projection ("MIP") of the three-dimensional MR image in which the image values have been scaled.

In accordance with another aspect of the invention, a bolus of contrast agent is administered to the patient's circulatory system in such a manner as to enhance the patient's blood vessels within the VOI. Then, in accordance with this aspect of the invention, a plurality of three-dimensional MR datasets (these will be referred to herein as "dynamic MR datasets") are acquired from the VOI, beginning with the administration of the contrast medium and continuing for a sufficiently long time to reflect contrast agent enhancement of all arterial and venous blood vessels within the VOI. These dynamic MR datasets, taken as a whole, in effect provide time-based information which, as explained above, can be used to distinguish arteries from veins (and indeed can be used to distinguish between different parts of a single artery or vein).

Advantageously, and if an intravascular contrast agent is available, a three-dimensional MR angiogram of the patient's VOI is acquired after the contrast agent has reached equilibrium. This in effect provides a high-quality three-dimensional image of the patient's vasculature. Then, for each voxel within the VOI, enhancement of that voxel as a function of time post administration of the contrast agent is computed based on the information derived from the dynamic 3D datasets. After such computation has taken place, parameters (advantageously, time-to-peak-enhancement, magnitude of peak enhancement, slope of signal enhancement as a function of time) that distinguish enhancement of voxels relating to the patient's arteries from enhancement of voxels relating to the patient's veins are selected and the intensity of each voxel in the three-dimensional MR angiogram is scaled in accordance with the selected parameters. Then, advantageously in accordance with the preferred embodiment of the invention, a maximum intensity projection ("MIP") reconstruction of the VOI is generated. Although an MIP reconstruction is presently preferred, it is not necessary; it may alternatively be advantageous to use some form of 3D surface rendering instead.

Advantageously, and in accordance with the preferred embodiment of the invention, the physician or technologist carries out the scaling step interactively while viewing the MIP reconstruction. This permits the physician or technologist to so adjust the display as to emphasize only the particular structure (vein, artery, or part(s) thereof) of interest. Further advantageously, the dynamic MR datasets are acquired rapidly to provide high temporal resolution. When so acquired, the dynamic MR datasets are of relatively low spatial resolution. If the contrast agent is of the intravascular type, a high-resolution three-dimensional MR angiogram can be acquired over a longer time. The voxel sizes of the dynamic MR datasets and the high-resolution MR angiogram are effectively normalized by spatially interpolating the dynamic MR datasets to correspond to the spatial resolution of the high resolution angiogram. In this manner, a signal enhancement curve is generated for every voxel in the high resolution angiogram.

BRIEF DESCRIPTION OF THE DRAWINGS

The invention will be better understood with reference to the accompanying exemplary and non-limiting drawings, in which.

DETAILED DESCRIPTION OF PREFERRED EMBODIMENTS

The preferred embodiment herein described is carried out on a conventional MR imager (not shown) using a three-dimensional pulse sequence (also not shown). The type of imager, and the pulse sequence used, are not part of the invention. Furthermore, although the preferred embodiment is illustrated using a VOI that includes the heart and cardiac blood vessels, this is only because cardiac MRA is of particular interest. The VOI is not a part of the invention.

The preferred embodiment of the invention assumes that a bolus of an MR contrast agent is administered to the patient. Although the contrast agent may be one of the currently commercially available Gadolinium (Gd)-based MR contrast agents, it is particularly advantageous if the contrast agent is one of the new intravascular agents currently under development, such as MS-325 manufactured by Epix Medical, Inc. Conventional Gd-based MR contrast agents diffuse into tissue through the capillaries, but the new under-development intravascular agents do not do so; they remain in the patient's vascular structure.

In a first step 10 (see FIG. 5) in accordance with the preferred embodiment of the invention, a bolus of the contrast agent is administered (as by injection) to the patient's circulatory system. As is known to persons skilled in the art, the bolus will travel through the patient's circulatory system and will progressively diffuse (i.e. will become less and less bolus-like). At some point, the contrast agent will reach equilibrium within the patient, i.e. will be evenly distributed in the patient's circulatory system within the VOI, where it will uniformly enhance the arteries and veins within the VOI.

Figure 5:
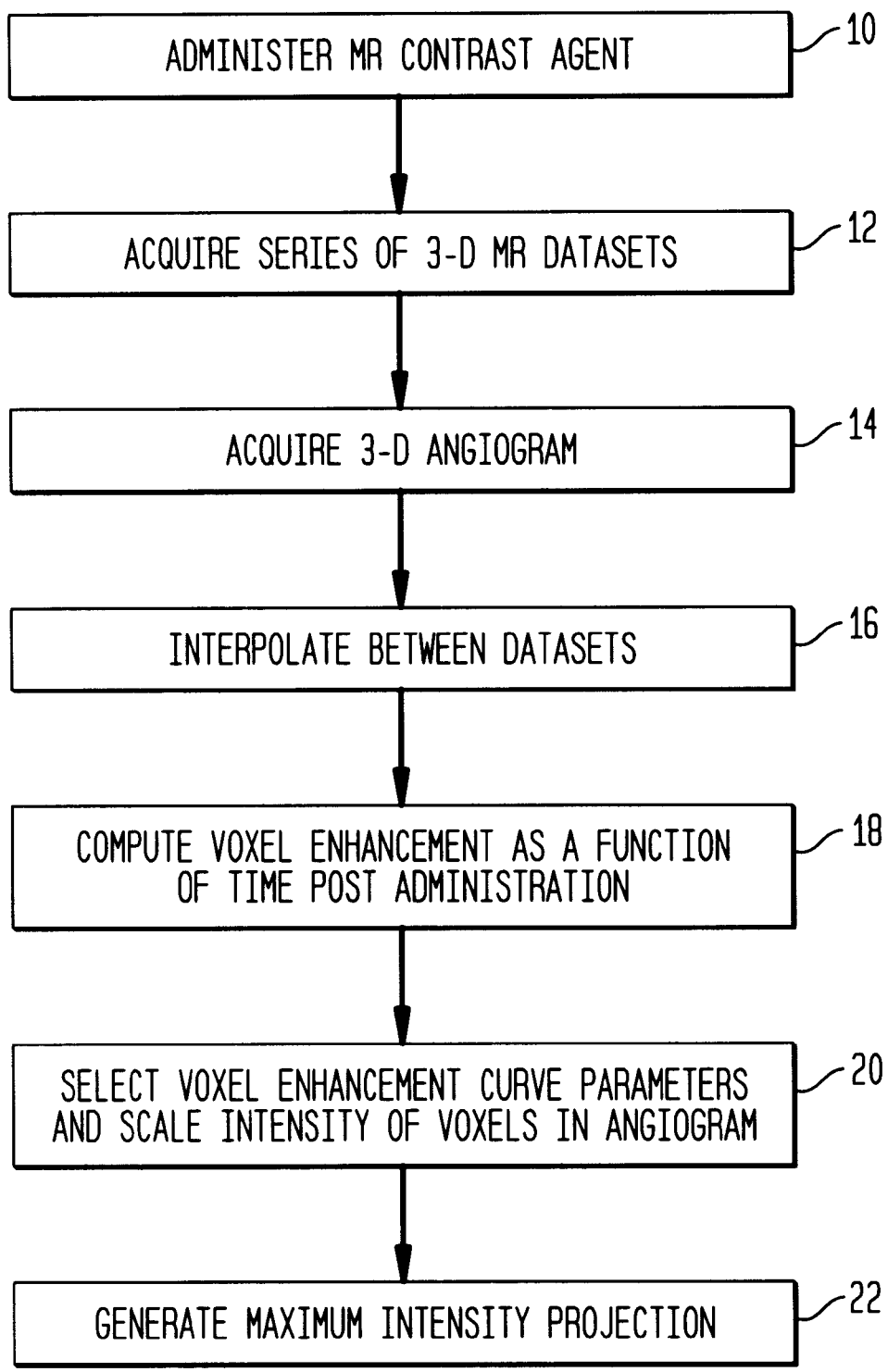
FIG. 5 is a flow chart of the preferred embodiment of the invention.

After the bolus of contrast agent has been administered, a series of three-dimensional MR datasets ("dynamic MR datasets") is acquired from the VOI (see step 12 in FIG. 5). In this example, seven such dynamic MR datasets are acquired, and each acquisition is two seconds long, but this is not required. There may be more or fewer dynamic MR datasets and each may be shorter or longer than two seconds. (A person skilled in the art can select the number and duration of the dynamic MR datasets in accordance with the study being carried out.) Indeed, the dynamic MR datasets need not be acquired for identical periods of time and need not be evenly spaced apart; this is convenient but unnecessary. The purpose of acquiring the dynamic MR datasets is to acquire information about how voxels in the VOI are enhanced as a function of time.

Figure 1:
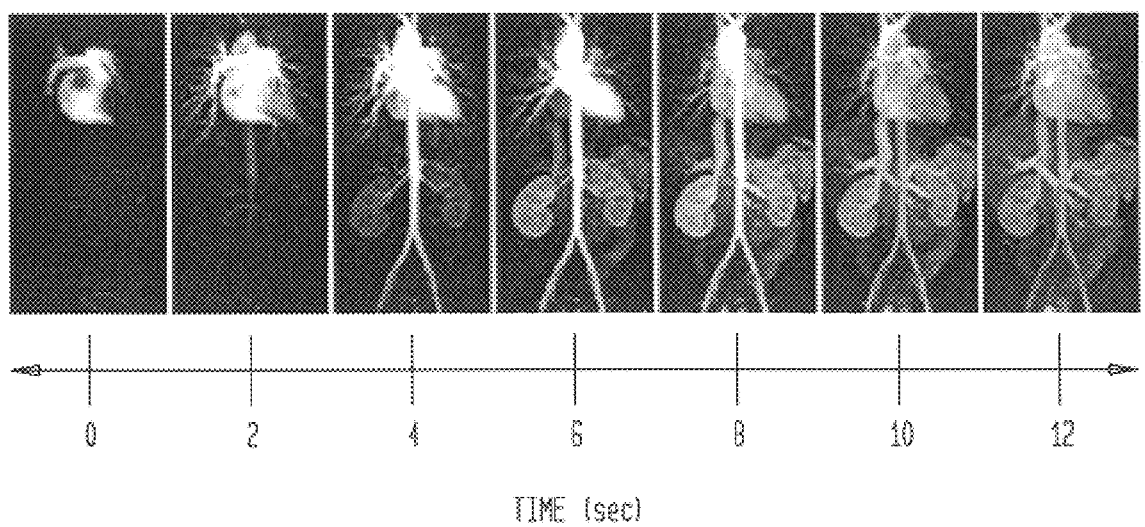
FIG. 1 schematically illustrates acquisition of a series of low-resolution three-dimensional MR datasets of the VOI in accordance with the preferred embodiment of the invention.

As can be seen from FIG. 1, differences between the dynamic MR datasets represent the progress of the contrast agent within the VOI as a function of time. Because in accordance with the preferred embodiment each dataset is acquired relatively quickly, the dynamic MR datasets are of comparatively low resolution, i.e. the acquired MR data is comparatively coarse and relates to comparatively large voxels within the VOI.

Figure 2:
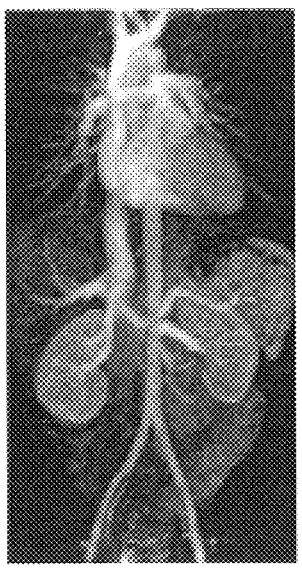
FIG. 2 schematically illustrates a high resolution three-dimensional angiogram of the VOI obtained after contrast agent has equilibrated throughout the circulatory system.

In further accordance with the preferred embodiment of the invention, the next step 14 (FIG. 5) is to acquire a high-resolution three-dimensional MR angiogram of the VOI (FIG. 2) once the contrast agent has reached equilibrium. In such an angiogram, all arteries and veins are enhanced and arteries cannot be visually distinguished from veins. As will be seen below, this angiogram is used as the source of information relating to that portion of the patient's anatomy that is within the VOI. Because the angiogram is of high resolution, the acquired MR information is comparatively fine and relates to comparatively small voxels within the VOI. Although acquisition of such a high-resolution angiogram is not necessarily required, it is advantageous because it allows the physician or technologist to view a higher quality image.

Figure 3:
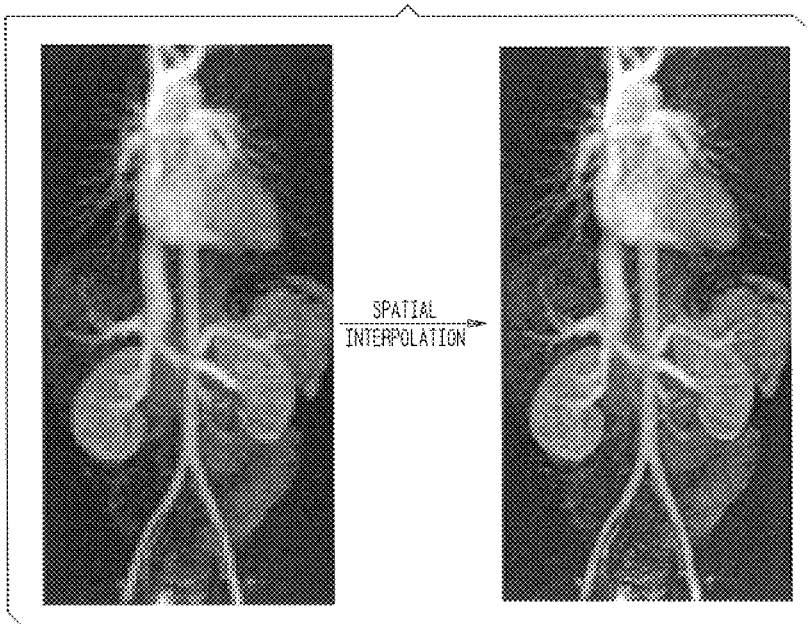
FIG. 3 schematically illustrates spatial interpolation of the low-resolution three-dimensional MR datasets in accordance with the preferred embodiment of the invention.

When, as in the preferred embodiment of the invention, there is a difference in the resolutions of the MR datasets and the three-dimensional MR angiogram, it is necessary to recast the acquired data so that it is in a consistent form. Advantageously, and in accordance with the preferred embodiment of the invention, this is done by spatially interpolating the MR datasets (step 16 in FIG. 5); such spatial interpolation techniques are known to persons skilled in the art. The result of this spatial interpolation is to normalize voxel size so that, as explained below and illustrated in FIG. 3, the time-based intensity information from the MR datasets can easily be exported to the MR angiogram. As is known to persons skilled in the art, mapping of temporal information from the low spatial resolution dynamic datasets onto a higher resolution MR angiogram cannot be properly carried out without two other steps, namely "image registration" and "thresholding". "Image registration" refers to compensation for patient movement during acquisition of the dynamic MR datasets, and "thresholding" refers to the process of excluding certain voxels from consideration during later computational steps. (Such exclusion is necessary when the detected enhancement of such voxels cannot be clearly identified as originating from something other than noise.) These steps are not described here; they are not part of the present invention.

In accordance with the preferred embodiment of the invention, for each voxel within the VOI, enhancement of that voxel as a function of time post administration of the contrast agent is computed (step 18 in FIG. 5). Advantageously, this is done using conventional curve-fitting techniques; such techniques are known to persons skilled in the art. Exemplary results of such effort are shown in FIG. 4.

Figure 4:
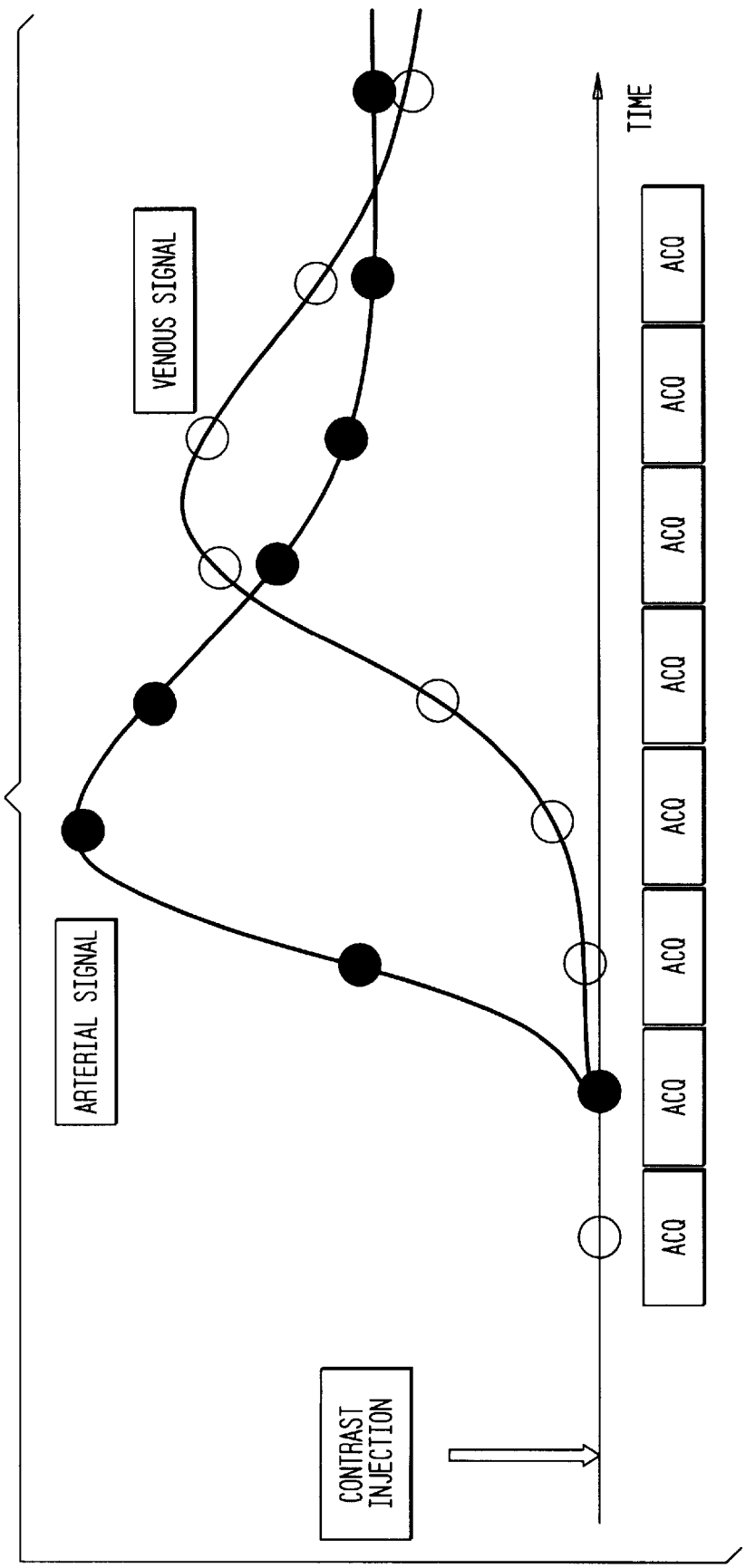
FIG. 4 schematically illustrates time-based voxel enhancement curves in accordance with the preferred embodiment of the invention.

The curves shown in FIG. 4 can be distinguished using various mathematical parameters. For example, because the bolus of contrast agent passes through the arteries before it passes through the veins, the time-to-peak enhancement of voxels in the patient's arteries is shorter than the time-to-peak enhancement of voxels in the patient's veins. Furthermore, because the bolus diffuses as it progressively moves through the patient's circulatory system, the peak enhancement of arterial voxels is greater than the peak enhancement of venous voxels. Consequently, it is possible to distinguish arterial voxels from venous voxels by e.g. sorting them on the basis of their time-to-peak enhancement, magnitude of peak enhancement, etc. Because time-to-peak and peak enhancement can be combined into the single parameter of "slope" of the enhancement curve, such slope can also or alternatively be used as a basis for distinguishing arterial voxels from venous voxels. Other parameters can also be used (alone, or together with other parameters).

Let it be assumed that a radiologist wishes to view an MR image of a VOI in which a portion of patient's artery is visually emphasized. Voxels relating to this portion can be specified by identifying those voxels in which e.g. the time-to-peak enhancement, the magnitude of peak enhancement, etc. meet appropriate criteria. Although voxels so identified actually relate to voxels in the dynamic MR datasets, because of the above-described interpolation and registration steps they can be mapped to corresponding voxels in the MR angiogram. Then, the intensity of the voxels in the MR angiogram can be scaled in accordance with the selected parameters. For example, the image intensity of the identified voxels can be set to maximum. This will cause the selected arterial portion to appear bright in the MR angiogram. (See step 20 in FIG. 5.) The degree and manner in which voxel intensity depends on enhancement curve parameters can be varied to advantageously depict a single anatomical portion of the circulatory system. Voxels can be made brighter or dimmer depending on the value of some function of the enhancement curve parameters.

In accordance with the preferred embodiment, a Maximum Intensity Projection ("MIP") is then generated (step 22 in FIG. 5), using the MR angiogram in which the image intensities have been scaled as described above. (MIP generation is known to persons skilled in the art.) This produces an image in which the vascular structure of interest is visually emphasized.

Advantageously, the above-referenced scaling step is carried out in an interactive manner, i.e. the radiologist modifies the selected parameters after viewing the MIP image to make the displayed image more appropriate.

While one or more preferred embodiments have been described above, the scope of the invention is limited only by the following claims:

I claim:

1. A method of a) acquiring three-dimensional MR data from a patient's arteries and veins within a volume of interest (VOI) made up of voxels and b) displaying an image reconstructed from such three-dimensional MR data in such a manner as to visually distinguish the arteries from the veins, comprising:

administering a bolus of an intravascular MR contrast agent to the patient's circulatory system in such a manner as to enhance the blood vessels;

acquiring a plurality of three-dimensional dynamic MR datasets from the VOI, said dynamic dataset acquisition beginning after administration of the contrast medium and continuing for a sufficiently long time as to reflect contrast agent enhancement of all arterial and venous blood vessels within the VOI;

acquiring a three-dimensional MR angiogram of the VOI after the contrast agent has reached equilibrium;

computing, for each voxel within the VOI, enhancement of that voxel as a function of time post administration of the contrast agent;

selecting parameters that distinguish enhancement of voxels relating to the patient's arteries from enhancement of voxels relating to the patient's veins;

scaling intensity of each voxel in the MR angiogram in accordance with the selected parameters; and generating a maximum intensity projection reconstruction of the VOI from the MR angiogram in which voxel intensity has been scaled.

2. The method of claim 1, wherein the scaling step is carried out interactively.

3. The method of claim 1, wherein the selecting step is carried out by selecting at least one parameter from the following list: time-to-peak-enhancement; magnitude of peak enhancement, and slope of signal enhancement as a function of time.

4. The method of claim 1, wherein the dynamic MR dataset acquiring step comprises the step of acquiring low resolution datasets, wherein the MR angiogram acquiring step is carried out at high spatial resolution, and further comprising the step of spatially interpolating the low resolution datasets and registering them with a high resolution angiogram.

5. The method of claim 1, wherein the computing step includes the step of interpolating, with respect to time, between magnitudes of voxel enhancement.

6. A method of a) acquiring three-dimensional MR data from a patient's vascular structure within a volume of interest (VOI) made up of voxels and b) displaying an image reconstructed from such three-dimensional MR data in such a manner as to permit a radiologist to selectively emphasize individual sections of the vascular structure, comprising:

administering a bolus of an intravascular MR contrast agent to the patient's circulatory system in such a manner as to enhance the vascular structure;

acquiring a plurality of low-resolution three-dimensional dynamic MR datasets from the VOI, said dynamic MR dataset acquisition beginning after administration of the contrast medium and lasting for a sufficiently long time as to reflect contrast agent enhancement of all vascular structure within the VOI;

acquiring a high-resolution three-dimensional MR angiogram of the VOI after the contrast agent has reached equilibrium;

spatially interpolating the dynamic MR datasets in such a manner as to equalize voxel size between the thus-interpolated dynamic MR datasets and the angiogram;

computing, by interpolation between voxels in which enhancement has been measured, and for each voxel within the VOI, enhancement of that voxel as a function of time post administration of the contrast agent;

selecting enhancement-based parameters that distinguish enhancements of voxels relating to different portions of the patient's vascular structure;

scaling intensity of each voxel in the angiogram in accordance with the selected parameters so to emphasize sections of interest within the patient's vascular structure; and generating a maximum intensity projection reconstruction of the VOI from the MR angiogram in which voxel intensity has been scaled.

7. A method of a) acquiring three-dimensional MR data from a patient's vascular structure within a volume of interest (VOI) made up of voxels and b) displaying an image reconstructed from such three-dimensional MR data in such a manner as to permit a radiologist to selectively emphasize individual sections of the vascular structure, comprising the following steps:

administering a bolus of an intravascular MR contrast agent to the patient's circulatory system in such a manner as to enhance the vascular structure;

acquiring three-dimensional dynamic MR image data from the VOI in such a manner as to register, as a function of time, movement of the contrast agent through the vascular structure;

acquiring a high-resolution three-dimensional MR image of the VOI after the contrast agent has reached equilibrium in the VOI;

scaling the acquired dynamic MR image data in accordance with the individual sections to be selectively emphasized; and displaying the high-resolution three-dimensional MR image using image values taken from the scaled acquired dynamic MR image data.

8. A method of a) acquiring three-dimensional MR data from a patient's vascular structure within a volume of interest (VOI) made up of voxels and b) displaying an image reconstructed from such three-dimensional MR data in such a manner as to permit a radiologist to selectively emphasize individual sections of the vascular structure, comprising the following steps:

administering a bolus of a MR contrast agent to the patient's circulatory system in such a manner as to enhance the vascular structure;

acquiring three-dimensional dynamic MR image data from the VOI in such a manner as to register, as a function of time, movement of the contrast agent through the vascular structure;

computing enhancement of voxels in the VOI as a function of time;

scaling voxels in a three-dimensional MR image of the VOI in accordance with their computed enhancement as a function of time; and displaying the MR image using image values taken from the scaled voxels.

9. The method of claim 8, wherein the three-dimensional MR image is a high-resolution MR angiogram acquired after the contrast agent has reached equilibrium.

* * * * *